United States Patent
Baur et al.

[11] Patent Number: 5,931,871
[45] Date of Patent: *Aug. 3, 1999

[54] KIT OF PARTS FOR A MODULAR FEMUR HEAD PROSTHESIS, IN PARTICULAR, A REOPERATION PROSTHESIS, AND A FEMUR HEAD PROSTHESIS FROM SUCH A KIT OF PARTS

[75] Inventors: Nikolaus Baur, Flurlingen; Stefan Lamprecht, Birchwil, both of Switzerland

[73] Assignees: Allo Pro AG; Sulzer Medizinaltechnik AG, both of Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/695,520

[22] Filed: Aug. 12, 1996

Related U.S. Application Data

[63] Continuation of application No. 08/325,748, Oct. 19, 1994, abandoned.

[30] Foreign Application Priority Data

Oct. 21, 1993 [EP] European Pat. Off. ............. 93810738

[51] Int. Cl.⁶ ..................................................... A61F 2/36
[52] U.S. Cl. ................................................................ 623/23
[58] Field of Search ........................................ 623/18, 23

[56] References Cited

U.S. PATENT DOCUMENTS

| | | |
|---|---|---|
| 3,987,499 | 10/1976 | Scharbach et al. .................. 623/17 |
| 4,051,559 | 10/1977 | Pifferi . | |
| 4,520,511 | 6/1985 | Gianezio et al. ..................... 623/23 |
| 4,718,915 | 1/1988 | Epinette ................................ 623/23 |
| 4,795,473 | 1/1989 | Grimes ................................... 623/23 |

(List continued on next page.)

FOREIGN PATENT DOCUMENTS

| | | |
|---|---|---|
| 0 019 042 | 11/1980 | European Pat. Off. . |
| 0217034 | 4/1987 | European Pat. Off. ............ 623/23 |
| 0 304 756 | 3/1989 | European Pat. Off. . |
| 0382395 | 8/1990 | European Pat. Off. ............ 623/23 |
| 0 399 920 | 11/1990 | European Pat. Off. . |

(List continued on next page.)

*Primary Examiner*—David H. Willse
*Attorney, Agent, or Firm*—Townsend and Townsend and Crew LLP

[57] ABSTRACT

The kit of parts comprises a distal shaft part (2) and a neck part (3) which can be equipped with a joint ball (10), with the neck part being supported on the shaft part (2) by approximately rectangular shaped supporting surfaces (2c) and (3c) positioned transverse to the longitudinal axis (L) of the shaft part (2). The shaft part (2) and the neck part (3) are provided with prismatic guide surfaces (2d) and (3d) brought together in a form-fit and orientated parallel to the longitudinal axis (L), and are rigidly connected to each other by an extensible shaft screw (11) which can be elastically prestressed to carry a predetermined bending moment. The guide surfaces (2d) and (3d) are formed at a spigot extension (2b) of the shaft part (2) and at a complementary recess (3b) of the neck part (3), respectively. This design allows a form-fitted centering and accurate positioning of the neck part (3) on the shaft part (2) by the guide surfaces (2d, 3d) and, independent therefrom, a force-locked connection between the neck part (3) and the shaft part (2) by way of the supporting surfaces (2c, 3c) which can be clamped against one another with the bias force of the extensible shaft screw (11).

15 Claims, 1 Drawing Sheet

U.S. PATENT DOCUMENTS

| | | |
|---|---|---|
| 4,921,499 | 5/1990 | Hoffman et al. .......................... 623/16 |
| 5,026,399 | 6/1991 | Engelbrecht et al. ..................... 623/18 |
| 5,035,712 | 7/1991 | Hoffman ................................... 623/16 |
| 5,074,879 | 12/1991 | Pappas et al. ............................ 623/18 |
| 5,100,407 | 3/1992 | Conrad et al. ............................ 606/79 |
| 5,152,795 | 10/1992 | Sioshansi et al. ........................ 623/16 |
| 5,507,830 | 4/1996 | DeMane et al. .......................... 623/23 |

FOREIGN PATENT DOCUMENTS

| | | |
|---|---|---|
| 0592897 | 4/1994 | European Pat. Off. ................. 623/18 |
| 2580171 | 10/1986 | France ...................................... 623/23 |
| 2 605 514 | 4/1988 | France . |
| 2606273 | 5/1988 | France ...................................... 623/22 |
| 2 622 791 | 5/1989 | France . |
| 2 633 509 | 1/1990 | France . |
| 211137 | 6/1908 | Germany . |
| 2933230 | 3/1981 | Germany . |
| 3033227 | 4/1982 | Germany . |
| 3736304 | 5/1989 | Germany . |
| 3805303 | 6/1989 | Germany . |
| 4106876 | 9/1991 | Germany . |
| 8603962 | 7/1986 | WIPO ...................................... 623/23 |
| 91/06260 | 5/1991 | WIPO ...................................... 623/16 |

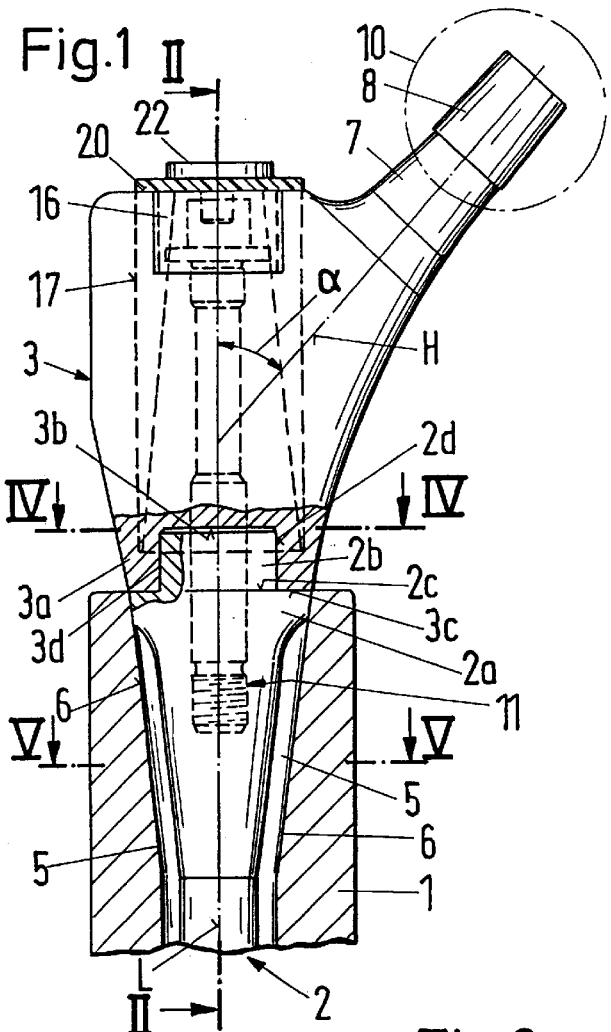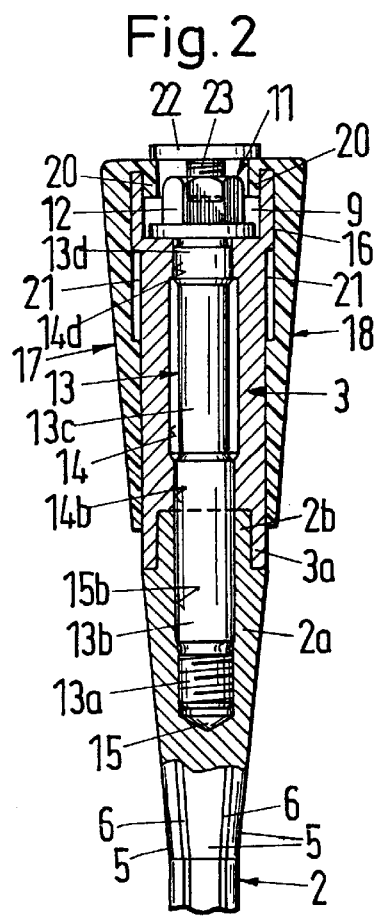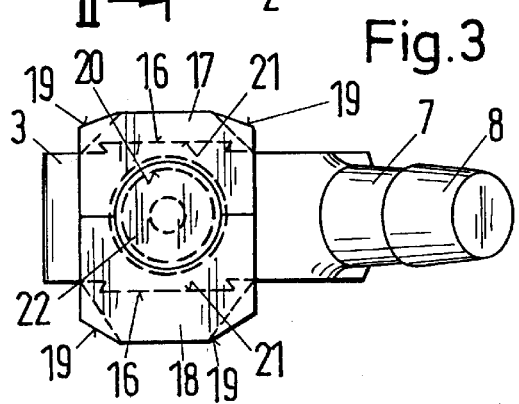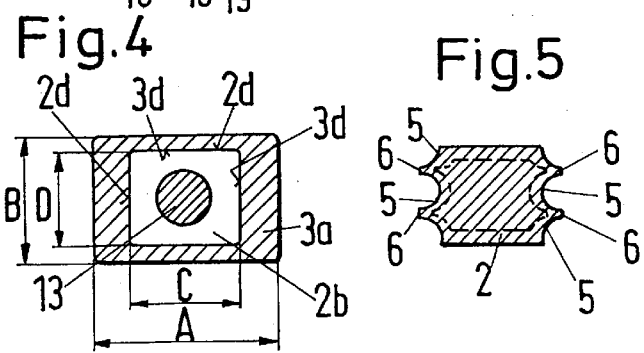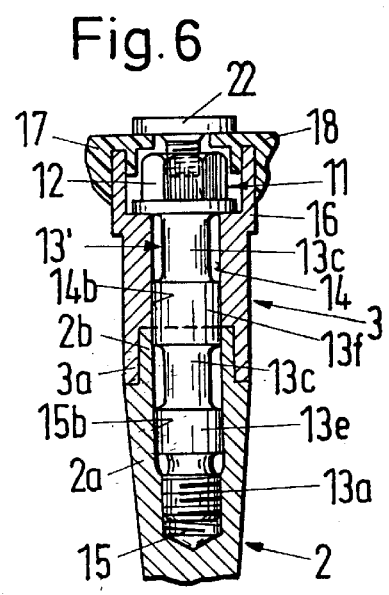

KIT OF PARTS FOR A MODULAR FEMUR HEAD PROSTHESIS, IN PARTICULAR, A REOPERATION PROSTHESIS, AND A FEMUR HEAD PROSTHESIS FROM SUCH A KIT OF PARTS

This is a continuation of Ser. No. 08/325,748 filed Oct. 19, 1994, now abandoned.

BACKGROUND OF THE INVENTION

The invention relates to a kit of parts for a modular femur head prosthesis, in particular a reoperation prosthesis comprising a distal shaft part to be anchored in a femur bone and a neck part which can be fixed to the proximal end portion of the shaft part by means of a screw connection, and can be equipped with an artificial ball.

Moreover, the invention relates to a femur head prosthesis assembled from such a construction kit.

A femur head prosthesis of the named kind is known from EP 0 399 920 A1 and comprises a shaft part having an outside thread and a proximal extension in the shape of a truncated cone and a neck part which can be mounted on the shaft part and which has a slip-on mandrel for the joint ball, with the mandrel being inclined with respect to the longitudinal axis of the shaft part. The neck part is held so that it can be clamped against the extension of the shaft part by a securing screw which can be screwed into an axial bore of the shaft part or of an insert part connected to it. The shaft part of the known endoprosthesis is provided with tongue-like, outwardly deployable segments in a longitudinal section of its axial bore. The segments can be clamped radially outwardly against the piece of femur surrounding the shaft part, in each case relative to two neighbouring fixed segments of the shaft part, by an adjusting means which can be introduced into the bore in the axial direction and which has wedge-shaped supporting surfaces. The main loading forces to be transferred to the femur are in each case respectively introduced into the femur shaft prosthesis by way of the joint ball which is laterally displaced with respect to the longitudinal axis of the shaft part. Accordingly, femur shaft prostheses of the type mentioned are stressed in each case by relatively large dynamic forces and bending moments. With the previous endoprostheses of the type mentioned, dynamic stresses or loads of this kind can lead to a loosening of the screw connection between the neck part and the shaft part and/or to a loosening of the anchoring of the shaft part in the femur bone and can, as a result, lead to high local stresses of the bone tissue, for example, in the region of a dowel-like spreading of the shaft part.

SUMMARY OF THE INVENTION

The object of the invention is to provide a kit of parts for a femur shaft prosthesis of the named kind which is improved in this respect and has a simple and robust method of construction, the kit of parts comprising a few favourably stressed components and ensuring a permanent connection between the neck part and the shaft part, as well as between the neck part and the femur, which remains unaffected by the dynamic stresses or loads in the implantation region.

According to the invention, this object is achieved in that the proximal end piece of the shaft part and of the neck part are provided with supporting surfaces which can be braced against one another and are positioned transverse to the longitudinal axis of the shaft part, and also with guide surfaces orientated in the direction of the longitudinal axis which can be brought together in a form-fitted manner in a defined coupling position of the two parts; and in that the screw connection includes an extensible shaft screw which can be elastically prestressed with a predetermined bias force.

The kit of parts formed according to the invention allows, on the one hand, a functional separation of the form-fitted, correct angle positioning of the neck part on the shaft part and, on the other hand, a force locked connection between the neck part and the shaft part inserted in the femur. Accordingly, the supporting surfaces of the neck part and the shaft part can be dimensioned for transmitting the clamping force of the extensible shaft screw corresponding to a predetermined greatest bending moment, and the guide surfaces can be dimensioned for transmitting relatively smaller transverse forces. A further advantage of the embodiment according to the invention is based on the fact that because the supporting surfaces of the neck part and the shaft part contact one another with a large surface pressure, the emergence of abraded particles arising between these parts can be prevented. The kit of parts according to the invention may comprise relatively few components which can be taken from a store comprising a plurality of shaft parts with different cross-sections and/or varying longitudinal dimensions, e.g., graded in a centimetre fashion, and a plurality of neck parts and extensible shaft screws, e.g. realized in two different dimensions, such that the kit of parts can be put together as a femur head prosthesis according to the given anatomical circumstances.

BRIEF DESCRIPTION OF THE DRAWINGS

Advantageous embodiments of the subject matter of the invention are set forth in the dependent claims.

Further features and details according to the invention will become evident from the following description of embodiments schematically represented in the drawings, in association with the patent claims. In the drawings there are shown:

FIG. 1 a partial view of a partly sectioned femur head endoprosthesis formed in accordance with the invention;

FIG. 2 a longitudinal section of the endoprosthesis corresponding to line II—II in FIG. 1;

FIG. 3 the endoprosthesis in a plan view;

FIG. 4 the endoprosthesis in a cross-section corresponding to line IV—IV in FIG. 1;

FIG. 5 a cross-section corresponding to line V—V in FIG. 1;

FIG. 6 a modified embodiment of an endoprosthesis in a representation corresponding to FIG. 2.

DESCRIPTION OF THE PREFERRED EMBODIMENTS

The femur head prosthesis according to FIGS. 1 to 5 is part of a reoperation prosthesis which is intended for use with patients as a second or third prosthesis, by whom, for some reason, a corresponding, earlier implanted endoprosthesis must be reoperated and replaced, for example, due to loosening of the embedding of the prosthesis in the bone tissue. The femur head prosthesis as represented, includes a distal shaft part 2 to be implanted in a femur bone 1 and a neck part 3. The distal shaft part 2 is to be embedded in the femur by way of bone cement, or as shown, without cement. The neck part 3 is made of a metal well-tolerated by the body, e.g. titanium, and can be mounted on the proximal end piece 2a of the distal shaft part. The neck part 3 is provided as a replacement-for a missing piece of bone which, in the example as shown, is the proximal end piece of the femur bone 1 which, especially in reoperation cases, must often be partly or, as shown, fully removed surgically, as a result of decomposition manifestations and demineralisation of the bone tissue. The shaft part 2 comprises a shaft body, conically tapered from its end piece 2a towards its distal end piece (not shown), which is to be inserted in the femur bone 1 in the direction of its longitudinal axis and a spigot-like extension 2b formed on the end piece which projects into a complementary recess 3b formed in the neck part 3. The shaft body 2 is provided over at least a part of its longitudinal extent with a plurality of longitudinal grooves 5 and between them a plurality of knife-like longitudinal ribs 6 which penetrate the bone tissue. On account of this the shaft body is held secure against turning in the femur bone 1.

The neck part 3 includes a main body corresponding to the surgically removed end of the femur bone 1 having a connecting part 3a to be attached onto the end piece 2a of the shaft part 2, and a mandrel 7 formed at the side and positionable so that it projects laterally with respect to the longitudinal axis L of the shaft part 2, with the longitudinal axis H of the mandrel or spigot 7 being inclined at an angle $\alpha$ with respect to the longitudinal axis L. The slip-on mandrel 7 ends in a cone 8 onto which, in known manner, a plastic ball 10 of a joint, represented by the chain-dotted line, can be mounted or plugged into position, with the plastic ball being laterally displaced with respect to the longitudinal axis. The end piece 2a of the shaft part 2, and at least the connecting part 3a of the neck part or, as shown, the whole main body of the neck part are each provided with a cross-section which is at least approximately rectangular in shape and with corresponding rectangular shaped supporting surfaces 2c and 3c which can be braced against each other and are positioned transverse to the longitudinal axis L. Each supporting surface 2c and 3c is arranged with a greater length dimension A directed in the lateral direction and a smaller breadth dimension B directed in the transverse direction. Likewise, the extension 2b of the shaft part 2 and the recess 3b of the neck part 3 are each provided with a corresponding approximately rectangular shaped cross-section and with side surfaces 2d and 3d which can be brought together in a form-fitted manner in the direction of the longitudinal axis L. In this way the shaft part 2 and the neck part 3 can be coupled with each other at a position defined with respect to the location of the joint ball 10.

The neck part 3 is fixed on the shaft part 2 by means of a screw 11 with an extensible shaft. The screw 11 comprises a head 12 to be supported countersunk in a recess 9 of the neck part 3, and a screw shaft 13 which extends through a bore 14 of the neck part 3 and an axial bore 15 of the shaft part 2. The screw shaft 13 includes a threaded section 13a to be screwed into a threaded bore of the shaft part 2 and two guide portions 13b and 13d thicker than said threaded screw section arranged at a distance from each other, as well as, an elastically prestressable, extensible section 13c connecting these two guide portions and having a cross-section, which, in known manner, is smaller than the core cross-section of the threaded section 13a. Cylindrical locating surfaces are formed on the guide portions 13b and 13d, and are intended to cooperate with corresponding fitting surfaces formed in the bores 14 and 15. According to FIG. 2, the guide portion 13d is formed close to the head 13 and cooperates with a bore section 14d of the neck part 3 while the guide portion 13b extends over the separating line between the neck part 3 and the shaft part 2 and cooperates with a bore section 14b of the neck part 3 and a bore section 15b of the shaft part 2.

By tightening the extensible shaft screw 11, the neck part 3 and the shaft part 2 are tensioned against one another with a bias clamping force which can be chosen as the peak force which corresponds to a predetermined greatest bending moment, introduced by a main load force acting by way of the joint ball 10 of a joint and applied at the neck part 3 in a laterally offset position with respect to the longitudinal axis L. The respective bias force is determined by the tightening torque for turning the extensible shaft screw 11 which can be defined, in a known manner, as a predetermined upper value on a torque wrench. The supporting force corresponding to the bias force is transmitted exclusively by the rectangular shaped supporting surfaces 2c and 3c surrounding the extension 2b and the recess 3b which are appropriately dimensioned to carry the dynamic forces and bending moments resulting from the main load.

When placing the neck part 3 onto the shaft part 2 these parts are centered and secured against turning by means of the guide surfaces 2d and 3d of the extension 2b and recess 3b respectively. An additional fine centering of the neck part 3 and of the shaft part 2 is achieved by the extensible shaft screw 11 by way of the cooperating locating surfaces of the guide portions 13b and 13d and the bore sections 14b, 15b and 14d respectively which, at the same time, ensures a guidance of the extensible section 13c of the reduced shaft screw 11 which is free of bending stresses. With the described arrangement, which enables a functional separation of the parts transmitting the longitudinal forces and the parts transmitting the transverse forces, a dimensionally stable connection which is rigid in bending is obtained between the rigid neck part 3 and the rigid end section of the shaft part 2 widened for the introduction of the forces to be transmitted in the lateral direction. With this embodiment a safe transmission of the dynamic forces and bending moments acting between the joint ball 10 and the shaft part 2 is ensured, even with large cyclical stresses.

The guide surfaces 2d and 3d brought together in a form-fit within the recess 3b are sealed outwardly by the supporting surfaces 2c and 3c surrounding them which are pressed together under a bias load such that, should the situation arise, abraded particles can be safely prevented from entering the surrounding tissue. On account of the supporting surfaces 2c and 3c of the shaft part 2 and the neck part 3 formed with a rectangular shaped hollow cross-section optimised to carry the greatest bending moment, together with the surface portions in the lateral edge parts which determine the moment of resistance of the cross-section, the loading which occurs on transmission of the pressure forces can, at the same time, be kept to surface pressure within predetermined limits. In order to obtain a design suitable for varying anatomical circumstances and which can be used as universally as possible, the respective supporting surfaces 2c and 3c can each have a length dimension A equal to around 20 mm to 30 mm and a breadth dimension B equal to around 10 to 15 mm. The extension 2b and the recess 3b each can have a corresponding measurement, e.g. a length measurement C equal to around 10 to 20 mm and a breadth measurement D equal to around 10 to 15 mm. It goes without saying that other dimensions for the end piece 2a and the connecting part 3a are possible which are matched to the respective anatomical circumstances.

As a substitute for a missing, surgically removed piece of a bone, front and back jaw-like filling bodies 17 and 18 can be fitted to the side walls of the neck piece 3 in accordance with the representation. These bodies can, as shown, be realised with bevelled edge parts 19 and varying decreasing thicknesses with respect to the neck piece 3, and can also be provided with means, not shown, for attaching muscles and ligaments thereon. The filling bodies 17 and 18 which can consist of metal or, as shown, of a synthetic material compatible with the body, are each equipped with a semi-circularly shaped collar portion 20 which can be attached on the proximal end piece of the neck part 3 and introduced into its recess 9. Moreover, the filling bodies 17, 18 can be equipped with a groove-like guideway 21, with which they can be pushed onto a guide section, formed on the side wall of the neck piece 3 in the form of a rail-like cam or track 16, and slid onto the relevant side wall in the direction of the longitudinal axis L until the collar portion 20 latches into the recess 9. The cam 16 and the guideway 21 can each be realised with a rectangular cross-section or, as shown, with a cross-section in the form of a dovetail. According to another embodiment, the guideways 21 can be formed on the neck piece 3 and the corresponding guide sections formed on the filling bodies 17, 18.

For the axial securing of the filling bodies 17 and 18 which are centered by the shoulder part 20 and guided sideways by the cams 16, a cap 22 can be provided which covers the recess 9. The cap has a threaded stem 23 which can be screwed into the screw head 12 and is tensioned against the collar portion 20. The cap 22 prevents at the same time the growth of tissue into the recess 9. The design of the filling bodies 17 and 18 and of the cap 22 as described, permits the operating surgeon to select the filling bodies 17, 18, corresponding to the respectively prevailing anatomical circumstances, from a supply of filling bodies made available in varying designs. It also permits the fixing of the filling bodies 17, 18 onto the already implanted neck piece 3 during an advantageous later stage in the operation.

An embodiment is also possible in which only one of the filling bodies 17 and 18 is fixed on the neck piece 3. Moreover, a suitably formed filling body can also be fixed to the lateral side wall of the neck piece 3. The embodiment according to FIG. 6 substantially corresponds to the embodiment described above, with the neck piece 3 having a smaller overall height and the extensible shaft screw 11 having a correspondingly shorter screw shaft 13' than in the example of FIGS. 1 and 2. The screw shaft 13' has two elastic prestressable extensible portions 13c and two guide portions 13e and 13f, with the guide portion 13e connected to the threaded portion 13a cooperating exclusively with the bore section 15b of the shaft part 2 and with the guide portion 13f positioned between the two extensible portions 13c extending over the partition line separating the neck piece 3 and the shaft piece 2 and cooperating with the upper end of the bore section 15b of the shaft part 2 and the lower end of the bore section 14b of the neck piece 3. In this embodiment, a fine centering of the shaft part 2 and the neck part 3 is achieved by the guide portion 13f as well as a stressing of the extensible shaft screw 11 which is substantially free from bending.

Numerous modified embodiments of the invention are possible. Instead of the illustrated embodiment having approximately rectangular support surfaces 2c and 3c, which are especially suited for the absorption of bending stresses, an embodiment is also possible having corresponding or, e.g., approximately circular or oval supporting surfaces. Similarly, instead of the illustrated rectangularly shaped projection 2b and the complementary recess 3b, a corresponding projection, e.g., a cylindrical or spherical projection and a complementary recess can be provided, as well as a centering element arranged outside of this recess. Such a centering element permits a corresponding correct angle positioning of the neck part 3 on the shaft part 2.

To summarise, the invention can be described as follows:

The kit of parts comprises a distal shaft part 2 and a neck part 3 which can be equipped with a joint ball 10, with the neck part being supported on the shaft part 2 by approximately rectangular shaped supporting surfaces 2c and 3c positioned transverse to the longitudinal axis L of the shaft part 2. The shaft part 2 and the neck part 3 are provided with prismatic guide surfaces 2d and 3d brought together in a form-fit and orientated parallel to the longitudinal axis L, and are rigidly connected to each other by an extensible shaft screw 11 which can be elastically prestressed to carry a predetermined bending moment. The guide surfaces 2d and 3d are formed at a spigot extension 2b of the shaft part 2 and at a complementary recess 3b of the neck part 3, respectively. This design allows a form-fitted centering and accurate positioning of the neck part 3 on the shaft part 2 by the guide surfaces 2d, 3d and, independent therefrom, a force-locked connection between the neck part 3 and the shaft part 2 by way of the supporting surfaces 2c, 3c which can be clamped against one another with the bias force of the extensible shaft screw 11.

We claim:

1. An arrangement for securing a modular femur head prosthesis in a femur bone comprising:

a shaft having a longitudinal axis, a distal end portion adapted for insertion into the femur bone and a proximal end portion defining a support surface transverse to the longitudinal axis and a guide surface parallel to the longitudinal axis;

a neck having a proximal end portion adapted for receiving an artificial joint ball and a distal end portion defining a support surface transverse to the longitudinal axis of the shaft and sized to be pressed against the shaft support surface, the distal end portion further defining a guide surface parallel to the longitudinal axis and conforming to the shaft guide surface;

a fastener for coupling the neck to the shaft having an extensible screw that is elastically pre-stressed with a predetermined bias force, the extensible screw comprising first and second thickened guide sections separated from one another by an extensible section having a smaller transverse cross-section than the guide sections, the guide sections defining cylindrical outer locating surfaces, the shaft and the neck each defining a bore defining centering surfaces cooperating with the guide sections of the extensible screw;

at least one filler body affixed to a side wall of the neck and extending laterally therefrom for replacing a missing piece of femur bone, wherein the filler body comprises a collar fixed to the neck along the longitudinal axis of the shaft; and wherein the extensible screw further comprises a head, the proximal end portion of the neck defining a second recess for receiving the head and the collar of the filler body, the neck further comprising a cover element covering the recess for tensioning against the collar.

2. A femur head prosthesis adapted for implantation in a femur bone comprising:

a shaft having a longitudinal axis, a distal portion adapted for implantation into the femur bone and a proximal end portion defining a support surface substantially perpendicular to the longitudinal axis and a guide surface parallel to the longitudinal axis;

an artificial ball joint;

a neck having a proximal end receiving the artificial joint ball and a distal end portion defining a support surface substantially perpendicular to the longitudinal axis of the shaft and abutting against the shaft support surface, the distal end portion further defining a guide surface parallel to the longitudinal axis and conforming to the shaft guide surface; and a fastener coupling the neck to the shaft and having an extensible screw that is elastically pre-stressed with a predetermined bias force, the screw comprising a threaded section and first and second thickened guide sections separated from one another by an extensible section having a transverse cross-section which is smaller than a core cross-section of the threaded section.

3. A method for anchoring a femoral prosthesis into a femur bone of a patient comprising:

securing a distal end portion of a shaft into a cavity of the femur bone;

mounting a neck to a proximal end portion of the shaft by:
positioning a transverse support surface of a distal end portion of the neck against a transverse support surface of the proximal end portion of the shaft; and
pressing the transverse support surface of the distal end portion of the neck against the transverse support surface of the proximal end portion of the shaft;

conforming a guide surface of the distal end portion of the neck to a guide surface of the proximal end portion of the shaft such that the guide surfaces are parallel to a longitudinal axis of the shaft;

inserting an extensible screw through the neck into the proximal end portion of the shaft to press the neck against the support surface of the shaft; and tightening the extensible screw by means of a torque wrench with a bias force which is defined as a predetermined upper value of the tightening torque of the torque wrench, and which corresponds to a predetermined greatest bending moment introduced by a main load force applied at the neck in a laterally offset position with respect to the longitudinal axis of the shaft.

4. A femur head prosthesis comprising:

a neck portion having a proximal portion adapted for receiving an artificial joint ball, the neck portion defining a neck bore therethrough;

a shaft portion having a distal portion adapted for insertion into a femur bone, the shaft portion defining a shaft bore;

said neck and shaft portions having distal and proximal transverse support surfaces, respectively, transverse to the axis, said transverse support surfaces abutting one another;

the neck bore and the shaft bore meeting at a bore intersection and defining an axis;

the neck bore and the shaft bore defining a first common-diameter, centering surface at said bore intersection;

at least one of the neck bore and the shaft bore defining a second centering surface;

the neck portion having a fastener support surface oriented transverse the axis;

an elongate fastener comprising a head, engaging the fastener support surface, and a fastener shaft, extending through the neck bore and into the shaft bore; and said fastener shaft comprising:
a fastener portion secured to the shaft portion;
a first centering surface region sized and positioned to be adjacent to the first centering surface on both sides of said bore intersection;
a second centering surface region sized and positioned to be adjacent to the second centering surface; and
a reduced-diameter region between the first and second centering surface regions.

5. The prosthesis of claim 4 further comprising at least one filler body affixed to a side wall of the neck portion and extending laterally therefrom for replacing a missing piece of femur bone.

6. The prosthesis of claim 5 wherein the neck portion comprises at least one guide section substantially extending parallel to the axis, the filler body having a groove for receiving the guide section and coupling the filler body thereof.

7. The prosthesis of claim 5 wherein the filler body comprises a collar fixed to the neck portion along the axis.

8. The prothesis according to claim 4 wherein the neck portion has a distal end portion and the shaft portion has a proximal end portion.

9. The prothesis according to claim 8 wherein one of the proximal and distal end portions comprises a projection and the other of the proximal and distal end portions comprises a cavity housing the projection.

10. The prosthesis according to claim 9 wherein said projection and said cavity have other than round cross-sectional shapes.

11. The prosthesis according to claim 9 wherein said projection and said cavity have polygonal cross-sectional shapes.

12. The prosthesis according to claim 11 wherein said polygonal cross-sectional shapes are both rectangular.

13. The prosthesis according to claim 4 wherein said elongate fastener is a single screw.

14. The prosthesis according to claim 4 wherein said neck bore defines said second centering surface.

15. The prosthesis according to claim 4 wherein said shaft bore defines said second centering surface.

* * * * *